United States Patent [19]
Dold

[11] Patent Number: 4,868,801
[45] Date of Patent: Sep. 19, 1989

[54] SPRING WINDING GEARING INCLUDING A SAFETY MECHANISM AGAINST RACING FOR THE DRIVE ASSEMBLY OF A DEVICE

[75] Inventor: Michael Dold, Schönwald, Fed. Rep. of Germany

[73] Assignee: B. Braun Melsungen AG, Fed. Rep. of Germany

[21] Appl. No.: 112,385

[22] Filed: Oct. 22, 1987

[30] Foreign Application Priority Data

Oct. 30, 1986 [DE] Fed. Rep. of Germany ....... 3636948

[51] Int. Cl.$^4$ .............................................. G04B 1/00
[52] U.S. Cl. ..................................... 368/139; 185/39
[58] Field of Search .................................. 185/38, 39; 368/124–154

[56] References Cited

U.S. PATENT DOCUMENTS

| | | | |
|---|---|---|---|
| 3,293,922 | 12/1966 | Pittman, Jr. ........................... | 185/38 |
| 4,602,700 | 7/1986 | Szabo .................................... | 185/38 |
| 4,676,122 | 6/1987 | Szabo et al. ........................... | 185/38 |

Primary Examiner—Bernard Roskoski
Attorney, Agent, or Firm—Spensley Horn Jubas & Lubitz

[57] ABSTRACT

The invention relates to a spring winding gearing for the drive assembly of a device with a drive shaft biased by a coil spring and a drive controlling device acting on the drive shaft via at least one intermediate transmission. A first toothed wheel is firmly attached to the drive shaft, a pivotable locking pawl is provided for the first toothed wheel, which locking pawl is held in the disengaged position by a movable support member, and a second toothed wheel is arranged at the support member, which second toothed wheel cooperates with the first toothed wheel and, upon increased rotational speed of the first toothed which second toothed wheel cooperates with the first toothed wheel for releasing the locking pawl. In this manner, racing of the drive shaft in case of a broken axle and the like is prevented, and in order to realize malfunction in due time, the safety mechanism against racing can be checked manually.

7 Claims, 2 Drawing Sheets

4,868,801

SPRING WINDING GEARING INCLUDING A SAFETY MECHANISM AGAINST RACING FOR THE DRIVE ASSEMBLY OF A DEVICE

BACKGROUND OF THE INVENTION

1. Field of the Invention:

The invention relates to a spring winding gearing for the drive assembly of a device, especially a medical infusion apparatus, with a drive shaft biased by a coil spring and a drive controlling means acting on the drive shaft via an intermediate transmission.

2. Description of the Related Art:

Spring winding gearings are used when a part has to be moved regularly for an extended period of time in a mechanical manner and without a current source. This is the case for all kinds of clocks. Further, in an apparatus for continuous infusion, a coil mechanism of the drive assembly serves to advance the plunger of an injection syringe, the advance being controlled by a mechanical clockwork. Such a continuous infusion apparatus is described in U.S. Pat. 4,300,554.

All spring winding gearings or clockwork mechanisms suffer from the disadvantage that, if any part between the spring box and the drive controlling means beaks, the drive assembly rapidly races without control. This is because the coil spring, once disengaged from the drive controlling means, can freely relieve, thus releasing the stored energy at once. Of course, this effect is undesired in every kind of application of a spring winding gearing. In a continuous infusion apparatus or a similar medical apparatus this effect is angerous because the highly effective endogenous chemical substance and the medicament, respectively, which is contained in the injection syringe, can be entirely injected into the blood vessel system of a patient suddenly, instead of being continuously administered in small doses over an extended period of time.

SUMMARY OF THE INVENTION:

It is an object of the invention to provide a spring winding gearing with a safety means against uncontrolled racing of the drive shaft upon interruption of the operative connection between the coil spring and the drive controlling means.

This object and others are solved with the present invention wherein a first power transmission wheel is firmly attached to the drive shaft, a rotatable locking element is provided for the first power transmission wheel, which locking element is held in the disengaged position by a movable support member, and a second power transmission wheel is arranged at the support member. The second power transmission wheel cooperates with the first power transmission wheel and, upon increased rotational speed or acceleration of the first power transmission wheel, tangentially displaces the support member with respect to the first power transmission wheel to release the locking element.

These joint features provide a safety means in a spring winding gearing which in case of breaking, e.g., breaking of an axle, prevents the drive shaft from freely racing in that the locking element engages the power transmission wheel connected with the drive shaft and locks this wheel against rotation until the locking element is deliberately returned into its disengaged position and the movable support member has regained its initial position for holding the locking element. The second power transmission wheel arranged at the support member and cooperating with the first power transmission wheel serves as a brake. The brake acts against movement of the power transmission wheel at the drive shaft if a defect in the spring winding gearing results in an increase of the rotational speed of the power transmission wheel and a moment of rotation is building up at the second power transmission wheel. Tangential forces effected by the moment of rotation at the second power transmission wheel tangentially push the support member away from the first power transmission wheel at the drive shaft, and the rotating locking element, having lost its holding support, abuts the periphery of the first power transmission wheel, thus locking the gearing against further undesired free racing. When using the spring winding gearing in accordance with the present invention in a permanent injection apparatus, an undesired sudden emptying of the injection syringe upon defects in the gearing is reliably prevented, i.e., it is safeguarded that the fluid to be administered is not suddenly pumped into the patient because of a racing drive shaft.

The power transmission wheels can be toothed wheels (ratchet discs) or frictional wheels. In the first case, a locking pawl is used as a locking element, whereas in the second case a brake shoe serves as a locking element.

In an advantageous embodiment of the invention, the locking element and the support member are spring-loaded. A tension spring engages the locking element, keeping it drawn against the support member maintained in the holding position and, if the support member is removed from its holding position, causing the locking element to be swiveled against the periphery of the first power transmission wheel on the drive shaft. A spring, e.g., a spiral spring, acts on the support member and presses it against a stopper to maintain the support member in the holding position. The spring force is adjusted to that moment of rotation of the gearing element upon which the support member shall release the locking element.

A further considerable advantage of the invention comprises the possibility of testing the safety mechanism against racing by pulling back the winding-up element so as to realize possible malfunctions. Since the functional gearing is suitably connected to the spring by a slipping clutch, it is possible to manually actuate the safety mechanism against racing by overcoming the moment of rotation transmitted by the slipping clutch. In this manner, the safety mechanism against racing can be used in the field of medical technology.

In an advantageous embodiment of the invention, the second power transmission wheel cooperates with at least one transmission element. As a transmission element, a further power transmission wheel and/or a fan wheel and a fly wheel, respectively, can be provided at the support member. The transmission element serves to increase the moment of rotation at the second power transmission wheel if the output speed is particularly low or if the assembly is stopped as a result of small changes in the rotational speed. The fan wheel and the fly wheel are well adapted to generate high counterforces. The fan wheel is velocity-dependent and upon increased rotational speed causes a braking of the first power transmission wheel on the drive shaft, whereas the fly wheel is acceleration-dependent and, due to its inertia, upon changes in speed at once generates a high resistance against rotation of the first power transmission wheel on the drive shaft.

The support member can be a rotatable rocking part. By the moment of rotation caused at the second power transmission wheel, the rocking part is swiveled around its pivot point such that it moves beyond the reach of the locking element, thus releasing the locking element to engage the power transmission wheel on the drive shaft. Further, the support member can be constructed as a sliding carriage which is movable tangentially with respect to the first power transmission wheel and which is tangentially moved under the influence of the accelerated second power transmission wheel.

BRIEF DESCRIPTION OF THE DRAWINGS

An embodiment of the invention is diagrammatically shown in more detail with reference to the drawings in which.

DESCRIPTION OF THE PREFERRED EMBODIMENTS

Figure 1:
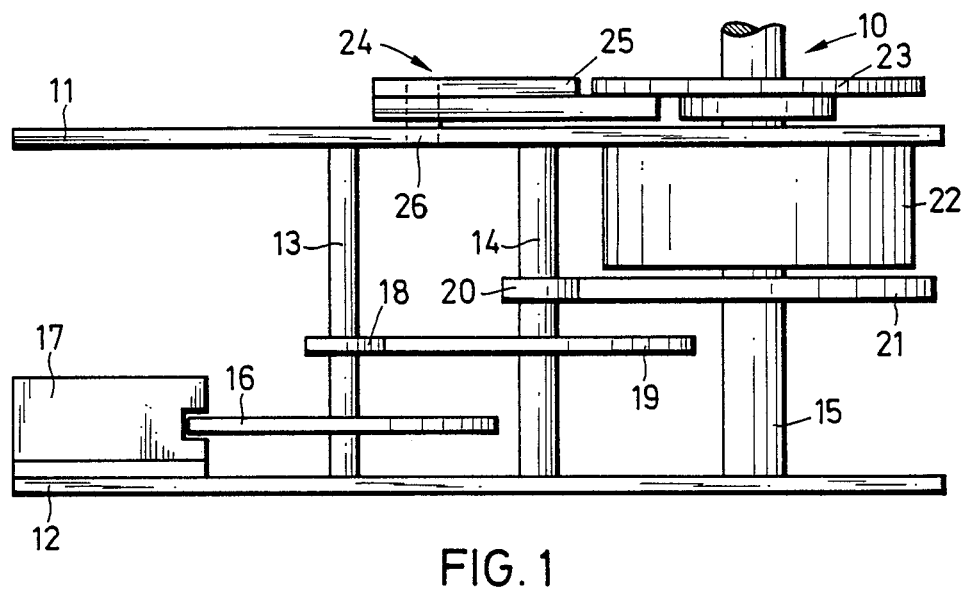
FIG. 1 shows a side view of a spring winding gearing.
Figure 2:
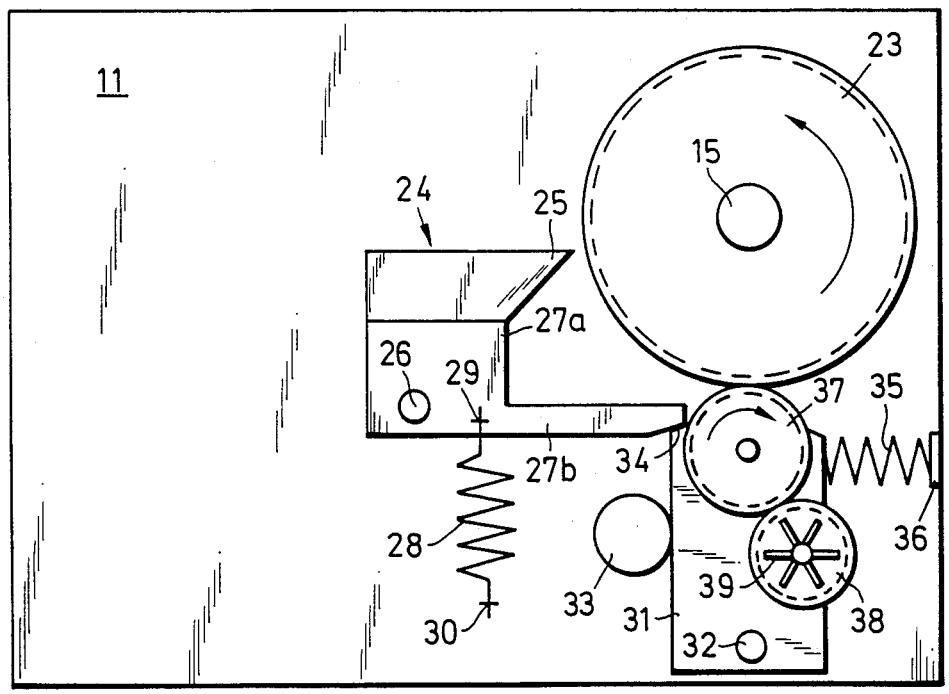
FIG. 2 shows a plan view of the spring winding gearing according to FIG. 1 in unlocked condition.

A drive-controlled spring winding gearing 10, e.g., for a continuous infusion apparatus, is provided with at least two spaced cover plates 11, 12 in which the ends of at least two axles 13, 14 and a drive shaft 15 are arranged. The axles and the shaft carry a plurality of sprockets. The axle 13 carries a minute wheel 16 cooperating with the output of the drive controlling means 17 which is represented by a little box containing the balance wheel with the escape anchor. Further, a smaller sprocket 18 is mounted on axle 13, forming an intermediate transmission (reduction gear) for drive shaft 15 with a larger sprocket 19 on axle 14. The number of the transmission means can also be smaller or larger. The connection between axle 14 and drive shaft 15 is provided by meshing sprockets 20 and 21 sprocket 21 on drive shaft 15 being considerably larger than sprocket 20 on axle 14. The drive shaft 15 is surrounded by a coil spring in a spring box 22, which coil spring maintains drive shaft 15 biased as long as it is wound.

The drive shaft 15 penetrates the cover plate 11 and has its outer portion tightly connected to a first toothed wheel 23. At the same plane, beside the comparatively large first toothed wheel 23, a locking pawl 24 is fastened to cover plate 11 for tilting movement upon a pivot point 26. The locking pawl 24 generally comprises a flat angle piece having a broad arm 27a directed upwardly, a thin long arm 27b extending outwardly from said broad arm and a body having a wedged tip 25 connected to arm 27a. The pivot point 26 is provided in the lower angle of arm 27a of the angle piece. The wedged tip 25 and the long arm 27b are facing toothed wheel 23. The angle piece of locking pawl 24 is acted upon by a tension spring 28 being fastened to the angle piece at 29 and to the cover plate 11 at 30. The fastening point 29 of tension spring 28 lies between the pivot point 26 of locking pawl 24 and the long arm 27b.

On cover plate 11, there is further provided a support member formed as a rocking part 31 to be swiveled at a pivot point 32. The rocking part 31 is formed as a rectangular plate which in vertical orientation (holding position) has one longitudinal edge abutting against a pin 33 perpendicularly protruding from cover plate 11 and has its upper edge portion 34 engaging under a bevel of long arm 27b of locking pawl 24 whereby the locking pawl is maintained in the disengaged position regarding the facing toothed wheel 23. The holding position of rocking part 31 is adjusted by a spring 35 the one end of which engages a side edge of rocking part 31 and the other end of which is fastened to cover plate 11 at 36. On one side surface of rocking part 31, a small toothed wheel 37 is rotatably supported. The toothed wheel 37 meshes with the gear rim of the larger toothed wheel 23 by which it is permanently rotated.

Figure 3:
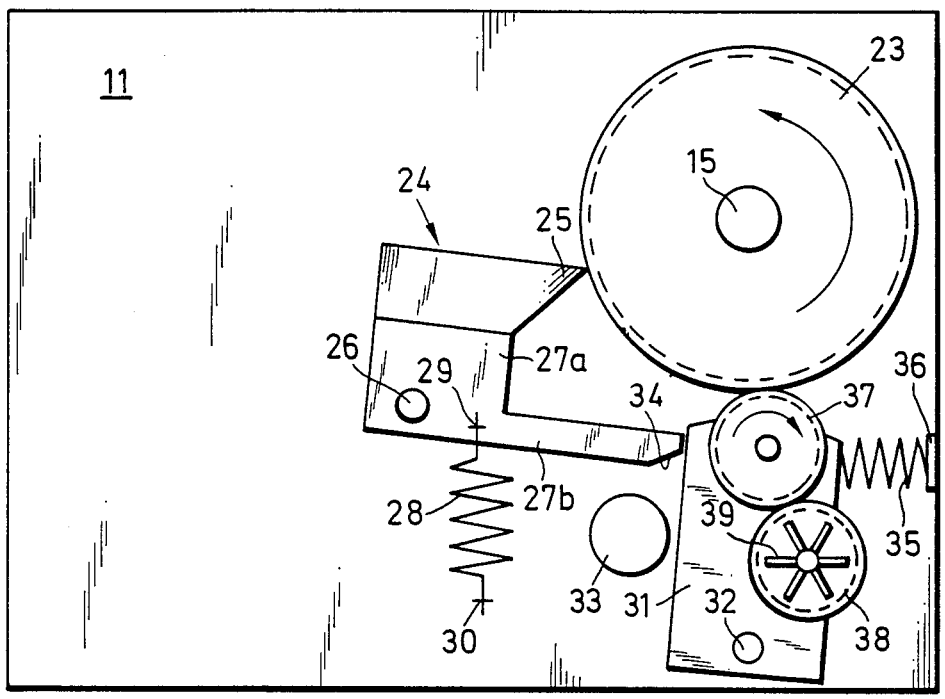
FIG. 3 shows the assembly according to FIG. 2 in locked condition.

If a defect in the spring winding gearing, e.g., breakage of the axles 13 or 14, leads to an increase of the rotational speed of toothed wheel 23 on drive shaft 15, a moment of rotation builds up on toothed wheel 37 and acts against the movement of toothed wheel 23. Since toothed wheel 37 is supported on rocking part 31, the rocking part now seeks to move against the force of spring 35. When the moment of rotation on toothed wheel 37 has become so large as to overcome the tension of spring 35, rocking part 31 moves away from pin 33 and is swiveled upon pivot point 32 into the position shown in FIG. 3. In this position, the central axle of toothed wheel 37 is no longer oriented vertically under the central axis of toothed wheel 23. The angular displacement of rocking part 31 releases arm 27b of locking pawl 24, and locking pawl 24 is pulled by tension spring 28. Thus, tension spring 28 turns around pivot point 26 while its wedged tip 25 engages the teeth of toothed wheel 23. In this manner, drive shaft 15 is locked against rotation, and there is effected protection against undesired free racing along with uncontrolled excess function of a part to be driven, e.g., a syringe plunger in a continuous infusion apparatus.

The function of the safety mechanism against racing can also be checked by simply turning back a winding-up wheel. Since the functional gearing is connected to the spring by a slipping clutch, the safety mechanism against racing can be hand-activated by overcoming the moment of rotation transmitted by the slipping clutch. To this purpose, a winding-up lever (not shown) is used to accelerate toothed wheel 23, i.e., raising its rotational speed such that snap-in of the locking pawl 25 is accomplished. By unlocking, the gearing is made ready for work again.

After checking the safety device, when restarting the gearing or after repair, the locking pawl 24 is returned to its disengaged position for example by a lever extending outwardly through cover plate 11. In this disengaged position, arm 27b rests on the edge of rocking part 31 which again maintains its vertical position under toothed wheel 23 in which position rocking part 31 is pushed against pin 33 by spring 35.

If the driving speed is particularly low or if the device shall be arrested due to small changes of the rotational speed of drive shaft 15, the moment of rotation at toothed wheel 37 is increased by at least one further toothed wheel 38 which is smaller than toothed wheel 37 and, being laterally displaced with regard to wheel 37, is arranged on rocking part 31 so as to mesh toothed wheel 37. In addition to toothed wheel 38, a fan wheel 39 can be arranged on the rotational axle of wheel 38 for increasing the counterforces at toothed wheel 37 and, depending on the velocity, effecting braking action when the rotational speed increases.

Similarly to the fan wheel 39, a fly wheel can be provided at toothed wheel 38. Upon changes of speed, the inertia of the fly wheel at once generates a high resistance. Alternatively, the toothed wheel 38 can be replaced by the fan wheel 39 or a fly wheel.

What is claimed is:

1. A spring winding gearing for aresting the rapid unwinding of a spring biased drive shaft, comprising:
    a first power transmission wheel mounted on said drive shaft;
    a second power transmission wheel;
    a rotatable locking element having an engaged and a disengaged position relative to said first power transmission wheel; and
    a movable support member for holding said second power transmission wheel in tangential contact with said first power transmission wheel, said support member having a first position wherein said locking element is held in said disengaged position and a second position wherein said locking element is allowed to move to an engaged position,
    said support member moving from said first position to said second position when said first power transmission wheel increases rotational speed or accelerates, and further comprising:
    a first spring operatively attached to said support member for holding said support member in said first position; and
    a second spring operatively attached to said locking element for assisting movement of said locking element to said engaged position.

2. A spring winding gearing according to claim 1, further comprising:
    at least one transmission element in tangential contact with said second power transmission element for increasing the moment of rotation of said second power transmission wheel.

3. A spring winding gearing according to claim 1, further comprising:
    at least one transmission element in tangential contact with said second power transmission element for increasing the moment of rotation of said second power transmission wheel.

4. A spring wheel gearing according to claim 2, wherein said transmission element comprises a fan wheel.

5. A spring winding gearing according to claim 2, wherein said transmission element comprises a fly wheel.

6. A spring winding gearing according to claim 1, wherein said support member comprises a pivotable rocking part.

7. A spring winding gearing according to claim 1, wherein said support member comprises a sliding carriage.

* * * * *